US009943494B2

(12) United States Patent
Summar et al.

(10) Patent No.: US 9,943,494 B2
(45) Date of Patent: Apr. 17, 2018

(54) METHODS AND COMPOSITIONS FOR TREATMENT FOR CORONARY AND ARTERIAL ANEURYSMAL SUBARACHNOID HEMORRHAGE

(75) Inventors: Marshall L. Summar, Brentwood, TN (US); Frederick E. Barr, Nashville, TN (US); Reid Carleton Thompson, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/331,678

(22) Filed: Dec. 20, 2011

(65) Prior Publication Data

US 2012/0088835 A1  Apr. 12, 2012

Related U.S. Application Data

(63) Continuation of application No. 12/322,434, filed on Feb. 2, 2009.

(60) Provisional application No. 61/025,170, filed on Jan. 31, 2008.

(51) Int. Cl.
A61K 31/198 (2006.01)

(52) U.S. Cl.
CPC .................. A61K 31/198 (2013.01)

(58) Field of Classification Search
None
See application file for complete search history.

(56) References Cited

U.S. PATENT DOCUMENTS

| | | | |
|---|---|---|---|
| 4,196,265 A | 4/1980 | Koprowski et al. | |
| 4,458,066 A | 7/1984 | Caruthers et al. | |
| 4,554,101 A | 11/1985 | Hopp | |
| 4,683,195 A | 7/1987 | Mullis et al. | |
| 4,683,202 A | 7/1987 | Mullis | |
| 4,736,866 A | 4/1988 | Leder et al. | |
| 4,769,331 A | 9/1988 | Roizman et al. | |
| 4,965,188 A | 10/1990 | Mullis et al. | |
| 4,996,236 A | 2/1991 | Nakamura et al. | |
| 5,162,215 A | 11/1992 | Bosselman et al. | |
| 5,217,997 A | 6/1993 | Levere | |
| 5,279,833 A | 1/1994 | Rose | |
| 5,286,634 A | 2/1994 | Stadler et al. | |
| 5,286,739 A | 2/1994 | Kilbourn et al. | |
| 5,334,380 A | 8/1994 | Kilbourn et al. | |
| 5,374,651 A | 12/1994 | Kilbourn et al. | |
| 5,385,940 A | 1/1995 | Moskowitz | |
| 5,399,346 A | 3/1995 | Anderson et al. | |
| 5,489,742 A | 2/1996 | Hammer et al. | |
| 5,550,024 A | 8/1996 | Rothschild | |
| 5,550,316 A | 8/1996 | Mintz | |
| 5,573,933 A | 11/1996 | Seamark et al. | |
| 5,614,396 A | 3/1997 | Bradley et al. | |
| 5,625,125 A | 4/1997 | Bennett et al. | |
| 5,641,484 A | 6/1997 | Hung et al. | |
| 5,643,567 A | 7/1997 | Hung et al. | |
| 5,646,008 A | 7/1997 | Thompson et al. | |
| 5,648,061 A | 7/1997 | Bernstein et al. | |
| 5,651,964 A | 7/1997 | Hung et al. | |
| 5,741,957 A | 4/1998 | Deboer et al. | |
| 5,767,160 A * | 6/1998 | Kaesemeyer | 514/565 |
| 5,873,359 A | 2/1999 | Zapol et al. | |
| 5,874,471 A | 2/1999 | Waugh | |
| 5,891,459 A | 4/1999 | Cooke et al. | |
| 6,028,107 A | 2/2000 | Waugh | |
| 6,331,543 B1 | 12/2001 | Garvey et al. | |
| 6,337,321 B1 | 1/2002 | Cooke et al. | |
| 6,343,382 B2 | 2/2002 | Sciglia | |
| 6,346,382 B1 | 2/2002 | Summar et al. | |
| 6,358,536 B1 * | 3/2002 | Thomas | 424/608 |
| 6,642,208 B2 | 11/2003 | Cooke et al. | |
| 6,646,006 B2 | 11/2003 | Cooke et al. | |
| 6,689,810 B2 | 2/2004 | Martin | |
| 6,743,823 B1 | 6/2004 | Summar et al. | |
| 8,188,147 B2 * | 5/2012 | Summar et al. | 514/565 |
| 2001/0056068 A1 * | 12/2001 | Chwalisz et al. | 514/21 |
| 2002/0013288 A1 | 1/2002 | Cooke et al. | |
| 2003/0026849 A1 | 2/2003 | Thomas | |
| 2003/0134332 A1 | 7/2003 | Boykin | |
| 2004/0235953 A1 * | 11/2004 | Summar | A61K 31/195 514/565 |
| 2006/0194728 A1 | 8/2006 | Killian et al. | |
| 2007/0026448 A1 | 2/2007 | Ramanathan et al. | |

(Continued)

FOREIGN PATENT DOCUMENTS

AU   34605 71 A   4/1973
CN   1946388 A    4/2007

(Continued)

OTHER PUBLICATIONS

NCT00201214, Citrulline for Children Undergoing Cardiopulmonary Bypass Surgery, Sep. 16, 2005, available at http://www.clinicaltrials.gov/ct2/show/NCT00335244?term=intravenous+citrulline&rank=4.*

NCT00335244, Intravenous L-Citrulline to Treat Children Undergoing Heart Bypass Surgery, Jun. 7, 2006, available at http://www.clinicaltrials.gov/ct2/show/NCT00335244?term=intravenous+citrulline&rank=.*

Fagan et al., L-Arginine Reduces Right Heart Hypertrophy in Hypoxia-Induced Pulmonary Hypertension, Biochemical and Biophysical Research Communications 1999, 254, 100-103 ("Fagan", of record).*

Benedetto et al., "Increased L-citrulline/L-arginine plasma ratio in severe preclampsia," Obstet Gynecol, vol. 96, No. 3, pp. 395-399 (Sep. 2000). (Abstract).

(Continued)

*Primary Examiner* — Svetlana M Ivanova
(74) *Attorney, Agent, or Firm* — Hunton & Williams LLP

(57) ABSTRACT

Methods and compositions for treating a complication associated with aneurysmal subarachnoid hemorrhage (SAH), the method comprising administering an effective amount of a nitric oxide precursor to a subject in need thereof. Methods and compositions for treating vasospasm, the method comprising administering an effective amount of a nitric oxide precursor to a subject in need thereof.

7 Claims, 1 Drawing Sheet

(56) References Cited

U.S. PATENT DOCUMENTS

| | | | |
|---|---|---|---|
| 2007/0184554 | A1 | 8/2007 | Teuscher et al. |
| 2008/0234379 | A1* | 9/2008 | Summar et al. ............ 514/564 |
| 2009/0197964 | A1 | 8/2009 | Summar et al. |
| 2009/0312423 | A1 | 12/2009 | Summar et al. |

FOREIGN PATENT DOCUMENTS

| | | |
|---|---|---|
| CN | 200580012693.5 | 3/2012 |
| GB | 2322551 | 9/1998 |
| WO | WO 99/18949 | 4/1999 |
| WO | WO 9918949 A1 * | 4/1999 |
| WO | WO 2005/082042 | 9/2005 |

OTHER PUBLICATIONS

Fagan et al., "L-arginine reduces 1-10 right heart hypertrophy in hypoxia-induced pulmonary hypertension", Biochemical and Biophysical Research Communications, vol. 254, No. 1, pp. 100-103, (Jan. 8, 1999).
Nelin et al., "L-arginine, but not D-arginine, increases nitric oxide production and vasodilates hypoxic neonatal pig lungs", FASEB Journal, vol. 18, No. 4-5, p. A327 (2004).
Office Action corresponding to European Patent Application Serial No. 06 005 642.1-2403 dated Jul. 25, 2011.
Office Action corresponding to U.S. Appl. No. 09/585,077 dated Jul. 3, 2002.
Office Action corresponding to U.S. Appl. No. 12/322,434 dated Apr. 5, 2011.
First Office Action for CN200980109147.1—dated Sep. 5, 2012(10 pages).
First Office Action for CN200980109147.1—dated Sep. 5, 2012 (2 pages)—Communication from Foreign Associate providing Frist Office Action.
Anggard (1994) Lancet 343(8907): 1199-1206.
Blau, et al. (1996) Physician's Guide to the laboratory Diagnosis of Metabolic Diseases, London, Chapman & Hall Medical [Table of Contents].
Erez, et al. (2011) Nature Medicine 17: 1619-1626.
Harlow & Lane, (1988) Antibodies A Laboratory Manual, Cold Spring Harbor Laboratory [Table of Contents].
Schwartz & Dayhoff (1978) Matrices for Detecting Distant Relationships, Atlas of Protein Sequence and Structure, National Biomed Res Foundation, 5(supp 3): 353-358.
Ruberti, et al. (1969) "Hepatoprotective Effect of an Association of Amino Acids of the Krebs-Henseleit Cycle—Clinical and Statistical Consideration" 50(5): 397-425.
Amin, et al. (2002) "Arginine supplementation prevents necrotizing enterocolitis in the premature infant." Journal of Pediatrics 140(4): 425-431.
Awrich, et al. (1975) "Hyperdibasicaminoaciduria, hyperammonemia, and growth retardation." Journal of Pediatrics 87(5): 731-738.
Barr (2007) J of Thoracic and Cardiovascular Surgery 134(2):319.
Aschner (2004) Pediatric Pulmonology 26: 132-135.
Baudouin, et al. (1993) "L-arginine infusion has no effect on systemic haemodynamics in normal volunteers, or systemic and pulmonary haemodynamics in patients with elevated pulmonary vascular resistance." British Journal of Clinical Pharmacology 36(1): 45-49.
Boeger, et al. (1996) "Differential systemic and pulmonary hemodynamic effects of L-arginine in patients with coronary artery disease or primary pulmonary hypertension." International Journal of Clinical Pharmacology and Therapeutics 34(8): 323-328.
Bronchopulmonary Dysplasia—PubMed Health website A.D.A.M. Medical Encyclopedia (2011) [Nov. 30, 2012] (3 pages).
Erez, et al. (2011) Nature Medicine 17(12): 1619-1626.
Fagan, et al. (1999) Biochemical and Biophysical Research Communications 254(1): 100-103.
Gardiner, et al. (1995) Crit Care Med, 23(7):1227-1232.
Hess "Use of Inhaled Nitric Oxide in the Hypoxic Newborn" (2005).
Hojo, et al. 1990, Cancer j, 3(1):14-19.
Fike, et al. (2000) Journal of Applied Physiology 88(5): 1797-1803.
McCaffrey, et al. (1995) Biology of the Neonate 67(4): 240-243.
Mitani, et al. (1997) Circulation 96(2): 689-697.
Mourani, et al. (2004) Am J Respiratory and Crit Care Med 170: 1006-13.
Mostovoy & Ivanov (2002) "Nitric oxide in the treatment of conditions accompanied by persistent pulmonary hypertension of newborns." Internet Journal "Medical Conferences" pp. 1-4.
National Heart Lung and Blood Institute website—What is Bronchopulmonary Dysplasia [Nov. 30, 2012] (2 pages).
Nelin, et al. (2004) FASEB Journal 18(4-5): A327.
"Persistierende fetale Zirkulation (PFC-Syndrom)" (2009).
Pulmonary Hypertension—PubMed Health website A.D.A.M. Medical Encyclopedia (2011) [Nov. 30, 2012] (5 pages).
Romero, et al. (2006) Cardiovascular Drug Reviews 24(3-4): 275-290.
Ruiz & Tejerina (1998) British Journal of Pharmacology 125: 186-192.
Russell, et al. (1998) Anesth Analg 87:46-51.
Saugstad (2003) Semin Neonatol. 8(1): 39-49 [Abstract].
Schulze-Neick, et al. (1998) Pediatric Anesthesia 87: 46-51.
Schulze-Neick, et al. (1999) Circulation 100:749-755.
Smith, et al. (2006) Journal of Thoracic and Cardiovascular Surgery 132(1): 58-65.
Suschek, et al. 2003, Circulation, 107(20):2607-2614.
Waugh, et al. (2001) J. Natl. Med. Assoc. 93(10): 363-371.
Ware, et al. (2013) Critical Care 17: R10.
Hecker, et al. 1990, Proc. Nat. Acad. Sci., 87: 8612-8616.
Harrison 1997, J. Clin. Invest., 100: 2153-2157.
Dioguardi (2011) J Nutrigenet Nutrigenomics 4: 90-98.
Genetics Home Reference "Lysinuric protein intolerance." (2011) [4 pages].
Hypertension, Pub Med Health, A service of the National Library of Medicine, National Institutes of Health, A.D.A.M. Medical Encyclopedia, Atlanta, GA, 2011.
Hypotension, Pub Med Health, A service of the National Library of Medicine, National Institutes of Health, A.D.A.M. Medical Encyclopedia, Atlanta, GA, 2011.
Kuhn et al. Circulation (2002) vol. 106, No. 19, Supplement pII 330 Abstract 1692.
Summar et al, Mol. Genet. Metab. (2004) 81 Suppl 1:S12-9.
Surdacki et al. Wien Klin Wochenschr. (1994) 106(16): 521-6.
Finckh, et al. Human Mutation (1998) 12(3): 206-211.
Shore, et al. The Journal of Biological Chemistry 254(9): 3141-3144.
AU 2009203177 (Jan. 31, 2012), Examination Rpt, 3 pgs.
CN 200980109150.3 (Jul. 3, 2012), Office Action.
EP 05723789.3 (Mar. 13, 2007), Search Report, 8 pgs.
JP 2006-554329 (Sep. 13, 2011), Office Action, pp. 8.
MX Pat Appln No. PA/a/2006/009468 (Jul. 6, 2011), Office Action, 4 pgs.
MX Pat Appln No. PA/a/2006/009468 (Mar. 1, 2012), Office Action, 5 pgs.
PCT IPRP (dated Sep. 8, 2006), PCT/US05/06081, 17 pgs.
SG 201005570-5 (Oct. 27, 2011), Search Rpt, 15 pgs.
U.S. Appl. No. 10/785,374 (Apr. 2, 2012), Interview Summary, 2 pgs.
U.S. Appl. 12/122,117 (Nov. 10, 2011), Advisory Action, 3 pgs.
U.S. Appl. No. 12/122,117 (Nov. 25, 2011), Interview Summary, 3 pgs.
U.S. Appl. No. 12/122,117 (Jan. 25, 2012), Notice of Allowance, 7 pgs.
U.S. Appl. No. 12/364,078 (May 23, 2011), Advisory Action.
Aschner, Chief of Neonatology and Professor of Pediatrics M.D., University of Rochester, 1981, (Medicine).
Asthma, The Merck Manual of Diagnosis and Therapy, 17th Ed. (1999), pp. 556-557, Merck Research Laboratories, Whitehouse Station, NJ.
Balasubramaniam et al. (2006), Am J Physiol Lung Cell Mol Physiol, 291(1):L119-L127.

(56) References Cited

OTHER PUBLICATIONS

Bourbon et al. (2005), Pediatric Res, 57:38R-46R.
Dikalova et al. (Jan. 2014), PLoS One, 9(1):e85730.
Dmitriev, "Optimal", Russian Language Dictionary, 2 pages. (w/trans).
Escobedo et al. (1982), Experimental and Mol Pathology, 37:323-334.
Fike et al. (2014), Acta Paediatr, 8 pgs.
Goodman et al.(Jan. 1988), J Pedi, 112(1):67-72.
Kinsella et al. (2014), J Pediatr, 6 pgs.
Lassala et al. (2009), J Nutri 139:660.
Lee et al. (1996) JPET, 276:353-358.
McDonald et al. (1997), J Bio Chem, 272(50):31213-31216.
Perrone et al. (2012), J Clin Neonat, 1(3):109-114.
Roblek et al. (May 2010), PLoS One, 5(5):e10604.
Stamler et al. (1992), Sci, 258(5090):1898-1902.
Stanker et al. (Jun. 1, 1986), Jimmunol, 136(11):4174-4180.
Vadivel et al. (2010), Pediatr Res, 68(6):519-525.
Vinten-Johansen et al. (1995), Int. J Cardiology, 50:273-281.
American Lung Association (2016) Bronchopulmonary Dsyplasia (12 pages).
American Lung Association (2016) Diagnosing and Treating Bronchopulmonary Dysplasia (12 pages).
American Lung Association (2016) Learn about Bronchopulmonary Dysplasia (19 pages).
Bernasconi et al. (2002) Pediatr Cardiol 4(1): 4-29.
Grover et al. Am J Physiol Lung Cell Mol Physiol (2005) 288: L648-L654.
Jung et al. J Neurosurg (2004) 101: 836-842.
Ladha et al. Am J Respir Cirt Care Med (2005) 172(6): 750-756.
Mayo Clinic (2014) Disease and Conditions: ARDS (5 pages).
Sallaam (2013) Persistent Newborn Pulmonary Hypertension Medscape (7 pages).

* cited by examiner

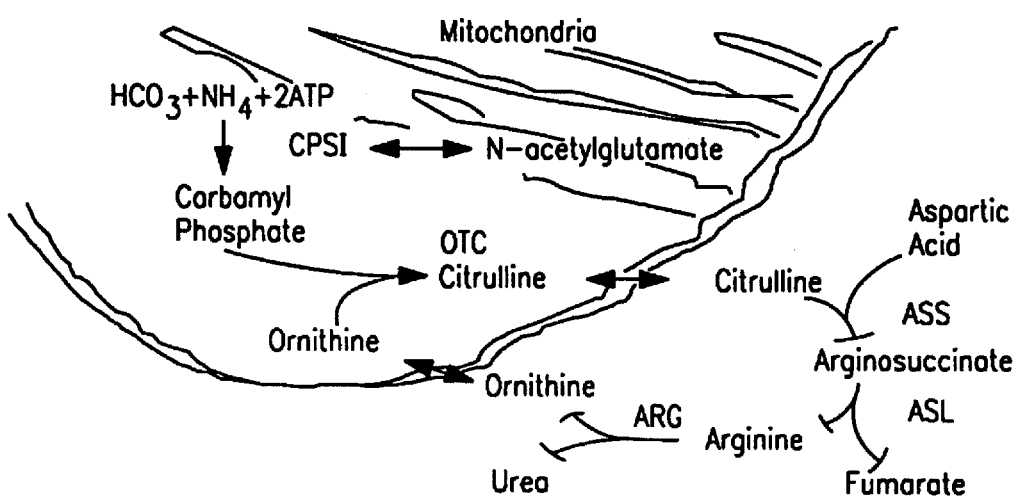

METHODS AND COMPOSITIONS FOR TREATMENT FOR CORONARY AND ARTERIAL ANEURYSMAL SUBARACHNOID HEMORRHAGE

RELATED APPLICATION INFORMATION

This continuation patent application is based on and claims priority U.S. patent application Ser. No. 12/322,434, filed Feb. 2, 2009, which claims priority to U.S. Provisional Patent Application Ser. No. 61/025,170, filed Jan. 31, 2008, the entire contents of both applications which are herein incorporated by reference.

TECHNICAL FIELD

The presently disclosed subject matter relates to the treatment of Aneurysmal Subarachnoid Hemorrhage (SAH), complications associated with SAH (including vasospasm), and vasospasm associated with atheroscelerosis, including but not limited to that associated with coronary arterial disease.

BACKGROUND

Aneurysmal Subarachnoid Hemorrhage (SAH) is one of the leading causes of morbidity and mortality associated with stroke worldwide. SAH is a neurological emergency characterized by extravasations of blood into spaces covering the central nervous system that are filled with cerebrospinal fluid. Several complications such as hydrocephalus, rebleeding, cerebral vasospasm, seizures, myocardial injury, and pulmonary edema can result from SAH.

SAH is a major concern throughout the world, with varying incidences of between about 1 and 96 incidents per 100,000 person/year (Batista da Costa Jr. et al. (2004) *Arq Neuro-Psiquiatr* (Sao Paulo) 62:245-249), with a worldwide incidence of about 10 per 100,000 person/year (Batista da Costa Jr. et al. (2004) *Arq Neuro-Psiquiatr* (Sao Paulo) 62:245-249). According to Suarez et al., SAH affects 21,000-33,000 people per year in the United States, and represents about 2-5% of all new strokes (Suarez et al. (2006) *N Engl J Med* 354:387-396). About 80% of cases of SAH result from rupture of an intracranial aneurysm, which itself is associated with significant risk of complications, including death. The peak age of incidence is 55-60 years, and about 20% occurs between the ages of 15 and 45 years. There is a gender difference in SAH, with a female preponderance characterized by a ratio of female to male patients ranging from 1.6-4.16:1. The incidence of SAH is also higher in African-Americans than in Caucasians.

Recent statistics indicate that about 30% of SAH patients die within the first 24 hours, and another 25-30% die within the following 4 weeks (Flett et al. (2005) *AJNR Am J Neuroradiol* 26:367-372). Besides the initial risks associated with SAH, a significant percentage of patients who have suffered SAH suffer from long-term cognitive impairment (Suarez et al. (2006) *N Engl J Med* 354:387-396), and thus SAH is associated with substantial impacts on health care resources.

While symptom management plays a major role in the treatment of SAH, there continues to be a long felt need for treatment strategies that address the underlying physiological bases for the development of secondary complications of SAH.

SUMMARY

The presently disclosed subject matter provides methods and compositions for treating SAH and/or associated complications in a subject. In some embodiments, an effective amount of a nitric oxide precursor is administered to a subject suffering from SAH and/or associated complications and/or at risk for suffering complications associated with SAH (e.g., vasospasm). In some embodiments, the nitric oxide precursor comprises at least one of citrulline, a precursor that generates citrulline in vivo, a pharmaceutically acceptable salt thereof, and combinations thereof. In some embodiments, the nitric oxide precursor, such as citrulline, is administered orally. In some embodiments, the nitric oxide precursor, such as citrulline, is administered intravenously. In some embodiments, the subject to be treated is a subject suffering from vasospasm. In some embodiments, the subject to be treated is a subject suffering from an acute condition associated with vasospasm.

The presently disclosed subject matter also provides methods and compositions for treating vasospasm. In some embodiments, the subject to be treated suffers from vasospasm associated with SAH. In some embodiments, the subject to be treated has suffered trauma that results in vasospasm (e.g., trauma that results in SAH). The methods can comprise administering to a subject in need thereof an effective amount of a nitric oxide precursor. In some embodiments, the nitric oxide precursor comprises at least one of citrulline, a precursor that generates citrulline in vivo, a pharmaceutically acceptable salt thereof, and combinations thereof. In some embodiments, the subject to be treated is suffering from vasospasm associated with SAH. In some embodiments, the nitric oxide precursor, such as citrulline, is administered orally. In some embodiments, the nitric oxide precursor, such as citrulline, is administered intravenously.

It is therefore an object of the presently disclosed subject matter to provide for treatment for SAH, vasospasm, and/or associated complications in a subject.

An object of the presently disclosed subject matter having been stated hereinabove, other objects will become evident as the description proceeds, when taken in connection with the accompanying drawings and examples as best described hereinbelow.

BRIEF DESCRIPTION OF THE DRAWINGS

FIG. 1 is a schematic of the urea cycle.

DETAILED DESCRIPTION

A considerable number of people worldwide are afflicted with Aneurysmal Subarachnoid Hemorrhage (SAH). The mortality rate for this condition is quite high, and even patients who survive SAH frequently experience dramatic reductions in their qualities of life. Current therapies in use can often prevent the death of a person who has experienced SAH if begun within an appropriate timeframe, but even successfully preventing that patient's death does not address the development of serious secondary complications. Therapies aimed at preventing secondary complications such as vasospasm and its sequelae, for example, are provided in accordance with aspects of the presently disclosed subject matter.

I. General Considerations

The in vivo synthetic pathway for arginine commences with ornithine. Ornithine is combined with carbamyl phosphate to produce citrulline, which in turn is combined with aspartate, in the presence of adenosine triphosphate (ATP), to produce argininosuccinate. In the final step, fumarate is split from argininosuccinate, to produce arginine. The degradative pathway for arginine is by the hydrolytic action of arginase, to produce ornithine and urea. These reactions form the urea cycle. The urea cycle serves as the primary pathway for removing waste nitrogen produced by the metabolism of endogenous and exogenous proteins, and is shown schematically in FIG. 1. In addition to its role in nitrogen clearance, the urea cycle is the body's intrinsic source of arginine which acts as a precursor of nitric oxide (NO), a potent vasodilator.

SAH typically results from rupture of a cranial aneurysm which results in leakage of blood into compartments of the nervous system that contain cerebrospinal fluid. Primary symptomology typically includes sudden onset of headache, which is usually very severe, nausea, vomiting, neck pain, photophobia, and loss of consciousness (Suarez et al. (2006) *N Engl J Med* 354:387-396), which is frequently associated with neurological deficits that become apparent on physical exam (Suarez et al. (2006) *N Engl J Med* 354:387-396). Hydrocephalus (20%), rebleeding (7%), cerebral vasospasm (46%), seizures (30%), hyponatremia (28%), myocardial injury (35%), and pulmonary edema (23%) occur in a significant percentage of patients, even if the damage to the underlying vessel(s) is repaired. These events also frequently lead to additional secondary complications, including seizures, pulmonary edema, cardiac arrhythmias, electrolyte disturbances, and neuropsychological complications such as problems with memory, mood, and neuropsychological function.

While the causes of the various sequelae of SAH are multifactorial, certain observations have been made. For example, decreased availability of nitric oxide in cerebral vessels has been observed, as has increased synthesis of endothelin or increase sensitivity of the arteries to this factor. Alterations in smooth muscle cells that promote a contracted state and activation of signal transduction mechanisms that can alter calcium sensitivity have also been reported. Additionally, increased thrombogenicity of the endothelium and/or platelet adhesion contributing to arterial dysfunction can occur, as can disruption of the blood brain barrier, inflammation, vasoconstriction, and injury to cerebral vessels of all sizes.

Given its devastating impact on patients, rapid diagnosis and treatment of SAH is critical. Typically, patients presenting with symptoms suggestive of SAH are subjected to head CT, which can detect the presence of SAH. If a subarachnoid hemorrhage is detected, FT angiography and/or cerebral angiography can locate an aneurysm, which is then repaired. If, however, the angiography is normal, CT angiography is typically repeated 1-3 weeks subsequent to initial presentation, optionally followed by brain, brain stem, and/or spinal cord imaging. In those cases where heat CT does not detect a subarachnoid hemorrhage, testing of cerebrospinal fluid obtained by lumbar puncture can also provide indicators of SAH, which then can be confirmed by angiography.

Once SAH is diagnosed, treatment generally includes securing of the aneurysm by neurosurgical clipping or endovascular coiling. Treatment of associated symptoms including, but not limited to hypertension, hyperthermia, hyperglycemia, and ischemia are performed as needed. Given that complications associated with SAH typically develop over the course of several weeks, a subject generally remains hospitalized for extended periods in order to provide continuous monitoring of the subject's condition.

II. Therapeutic Methods

The presently disclosed subject matter provides methods for treating SAH and/or associated complications in a subject. In some embodiments, an effective amount of a nitric oxide precursor is administered to a subject suffering from SAH and/or associated complications and/or at risk for suffering complications associated with SAH. Representative examples of such complications are disclosed herein above.

In some embodiments, the nitric oxide precursor comprises at least one of citrulline, a precursor that generates citrulline in vivo, a pharmaceutically acceptable salt thereof, and combinations thereof. See FIG. 1. In some embodiments, the nitric oxide precursor is selected from the group including, but not limited to, citrulline, arginine, or combinations thereof. In some embodiments, the nitric oxide precursor, such as citrulline, is administered orally. In some embodiments, the nitric oxide precursor, such as citrulline, is administered intravenously. In some embodiments, the subject to be treated is a subject suffering from vasospasm. In some embodiments, the subject to be treated is a subject suffering from an acute condition associated with vasospasm. Representative examples of such conditions are disclosed herein above.

In some embodiments, the subject suffering from a complication, such as vasospasm, suffers from relative hypocitrullinemia. The term "relative hypocitrullinemia" refers to a state in which the subject suffering from a complication has reduced plasma citrulline as compared to a subject not suffering from a complication.

In some embodiments, the subject suffers from hypocitrullinemia. In some embodiments the hypocitrullinemia is characterized by plasma citrulline levels of ≤37 µmol/liter, in some embodiments, ≤25 µmol/liter, in some embodiments, ≤20 µmol/liter, in some embodiments, ≤10 µmol/liter, in some embodiments, ≤5 µmol/liter.

The presently disclosed subject matter also provides methods and compositions for treating vasospasm. In some embodiments, the subject to be treated suffers from vasospasm associated with SAH. In some embodiments, the subject to be treated has suffered trauma that results in vasospasm (e.g., trauma that results in SAH). In some embodiments the vasospasm is associated with atherosclerosis in the subject. In some embodiments the atherosclerosis is associated with coronary artery disease in the subject, with carotid arterial disease in the subject, with peripheral arterial disease in the subject, and combinations thereof.

In some embodiments, the nitric oxide precursor comprises at least one of citrulline, a precursor that generates citrulline in vivo, a pharmaceutically acceptable salt thereof, and combinations thereof. See FIG. 1. In some embodiments, the nitric oxide precursor is selected from the group including, but not limited to, citrulline, arginine, or combinations thereof. In some embodiments, the nitric oxide precursor, such as citrulline, is administered orally. In some embodiments, the nitric oxide precursor, such as citrulline, is administered intravenously. In some embodiments, the subject to be treated is a subject suffering from vasospasm. In some embodiments, the subject to be treated is a subject suffering from an acute condition associated with vasospasm (e.g. ischemia and/or angina in coronary arterial disease).

In some embodiments, the subject suffering from a complication, such as vasospasm, suffers from relative hypocitrullinemia. The term "relative hypocitrullinemia" refers to a state in which the subject suffering from a complication has reduced plasma citrulline as compared to a subject not suffering from a complication.

As used herein, the phrase "treating" refers to both intervention designed to ameliorate a condition in a subject (e.g., after initiation of a disease process or after an injury) as well as to interventions that are designed to prevent the condition from occurring in the subject. Stated another way, the terms "treating" and grammatical variants thereof are intended to be interpreted broadly to encompass meanings that refer to reducing the severity of and/or to curing a condition, as well as meanings that refer to prophylaxis. In this latter respect, "treating" can refer to "preventing" to any degree, or otherwise enhancing the ability of the subject to resist the process of the condition, such as a subject at risk to suffer the condition.

The subject treated in the presently disclosed subject matter in its many embodiments is desirably a human subject, although it is to be understood that the principles of the presently disclosed subject matter indicate that the presently disclosed subject matter is effective with respect to all vertebrate species, including warm-blooded vertebrates such as mammals and birds, which are intended to be included in the term "subject". In this context, a mammal is understood to include any mammalian species in which treatment is desirable, such as but not limited to agricultural and domestic mammalian species.

Thus, provided is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like.

III. Pharmaceutical Compositions

An effective dose of a composition of the presently disclosed subject matter is administered to a subject in need thereof. An "effective amount" is an amount of a composition sufficient to produce a measurable response (e.g., a biologically or clinically relevant response in a subject being treated). Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. By way of example and not limitation, doses of compositions can be started at levels lower than required to achieve the desired therapeutic effect and to gradually increase the dosage until the desired effect is achieved. The potency of a composition can vary, and therefore an "effective amount" can vary.

After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, gender, severity and stage of symptoms, and the presence of additional deleterious physical conditions.

By way of additional examples, the amount of active ingredient that may be combined with the carrier materials to produce a single dosage form will vary depending upon the subject to be treated and the particular mode of administration. For example, a formulation intended for administration to humans can contain from 0.5 mg to 5 g of active agent compounded with an appropriate and convenient amount of carrier material which may vary from about 5 to about 95 percent of the total composition. For example, in a human adult, the doses per person per administration are generally between 1 mg and 500 mg up to several times per day. Thus, dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

The nitric oxide precursor is administered in some embodiments in a dose ranging from about 0.01 mg to about 1,000 mg, in some embodiments in a dose ranging from about 0.5 mg to about 500 mg, and in some embodiments in a dose ranging from about 1.0 mg to about 250 mg. The nitric oxide precursor can also be administered in some embodiments in a dose ranging from about 100 mg to about 30,000 mg, and in some embodiments in a dose ranging from about 250 mg to about 1,000 mg. A representative dose is 3.8 g/m2/day of arginine or citrulline (molar equivalents, MW L-citrulline 175.2, MW L-arginine 174.2).

Representative intravenous citrulline solutions can comprise a 100 mg/ml (10%) solution. Representative intravenous citrulline dosages can comprise 200 mg/kg, 400 mg/kg, 600 mg/kg, and 800 mg/kg. In some embodiments, for example but not limited to a 600 or 800 mg/kg dosage, the dose can be decreased by an amount ranging from 50 mg/kg and 100 mg/kg to mitigate observed undesired effects on systemic blood pressure. In some embodiments, doses can be administered one or more times during a given period of time, such as a day.

In some embodiments a pharmaceutical composition comprises an amount of citrulline effective to raise plasma citrulline level to treat a complication as disclosed herein in a subject. In some embodiments, the level is determined by comparing plasma citrulline levels in a subject to be treated to that observed in a subject not suffering from the complication. In some embodiments, the amount of citrulline is effective to raise plasma citrulline level in a subject to at least 5 μmol/liter, optionally at least 10 μmol/liter, optionally at least 20 μmol/liter, optionally at least 25 μmol/liter, and optionally about 37 μmol/liter.

In some embodiments, the presently disclosed subject matter provides pharmaceutical compositions comprising a nitric oxide precursor and a pharmaceutically acceptable carrier, such as a pharmaceutically acceptable carrier in humans. In some embodiments, the presently disclosed subject matter provides pharmaceutical compositions comprising citrulline or arginine in dosages as described above.

A composition of the presently disclosed subject matter is typically administered orally or parenterally in dosage unit formulations containing standard nontoxic pharmaceutically acceptable carriers, adjuvants, and vehicles as desired. The term "parenteral" as used herein includes intravenous, intramuscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic acceptable diluent or solvent, for example, as a solution in 1,3-butanediol.

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Exemplary carriers include neutral saline solutions buffered with phosphate, lactate, Tris, and the like.

In a representative embodiment doses can be administered to a subject several times during a relevant treatment period, including but not limited to 1, 2, 3, 4, 5, 6 or more dosages.

It will be understood, however, that the specific dose level for any particular subject will depend upon a variety of factors including the age, body weight, general health, sex, diet, time of administration, route of administration, rate of excretion, drug combination and the severity of the particular disease undergoing therapy.

EXAMPLES

The following Examples have been included to illustrate representative modes of the presently disclosed subject matter. In light of the present disclosure and the general level of skill in the art, those of skill will appreciate that the following Examples are intended to be exemplary only in that numerous changes, modification, and alterations can be employed without departing from the spirit and scope of the presently disclosed subject matter.

OVERVIEW OF EXAMPLES

While symptom management plays a major role in the treatment of SAH, there continues to be a long felt need for treatment strategies that address the underlying physiological bases for the development of secondary complications of SAH. For example, one of the key pathological mechanisms following aneurismal SAH is decreased availability of nitric oxide in cerebral vessels resulting in contraction of smooth muscles or vasospasm. By comparing plasma from patients with and without vasospasm it has been determined by the instant co-inventors there is a significant difference in citrulline levels such that patients with vasospasm have lower levels of citrulline as compared to patients without vasospasm. While it is not desired to be bound by any particular theory of operation, these results suggest that citrulline acting as a NO precursor can be a treatment for both SAH and coronary arterial disease through a similar mechanism of supporting vascular relaxation through restoring an adequate supply of citrulline which can act as a nitric oxide precursor amongst other actions.

Examples 1 and 2 present the results of assaying plasma levels of citrulline, ornithine, arginine, and nitric oxide in subjects with and without vasospasm. The samples were separated by 24 hours in time from collection. In Example 1, levels were assayed after early collection, and in Example 2, levels were assayed after late collection.

Example 1

Comparison of Plasma (Early Collection) in Patients without and with Vasospasm

| Parameter | Without vasospasm[1] | With vasospasm[1] | p-value |
|---|---|---|---|
| Citrulline (nM/ml) | 9.12 ± 1.2 | 5.66 ± 1.2 | 0.08 |
| Ornithine (nM/ml) | 31.66 ± 5.7 | 16.46 ± 3.4 | 0.04 |
| Arginine (nM/ml) | 34.88 ± 9.7 | 22.54 ± 4.3 | 0.14 |
| Nitric Oxide (µM) | 27.36 ± 4.8 | 30.72 ± 9.6 | 0.38 |

[1] n = 5; data expressed as mean ± standard error

Example 2

Comparison of Plasma (Late Collection) in Patients without and with Vasospasm

| Parameter | Without vasospasm | With vasospasm[1] | p-value |
|---|---|---|---|
| Citrulline (nM/ml) | 8.62 ± 1.2 | 4.81 ± 1.6 | 0.12 |
| Ornithine (nM/ml) | 42.60 ± 4.9 | 25.22 ± 6.5 | 0.06 |
| Arginine (nM/ml) | 47.76 ± 16 | 26.52 ± 9.0 | 0.14 |
| Nitric Oxide (µM) | 58.85 ± 39 | 48.01 ± 30 | 0.41 |

[1] n = 5; data expressed as mean ± standard error

REFERENCES

The references listed below as well as all references cited in the specification are incorporated herein by reference to the extent that they supplement, explain, provide a background for or teach methodology, techniques and/or compositions employed herein.

Batista da Costa Jr. et al. (2004) *Arq Neuro-Psiquiatr* (Sao Paulo) 62:245-249.
Suarez et al. (2006) *N Engl J Med* 354:387-396.
Flett et al. (2005) *AJNR Am J Neuroradiol* 26:367-372.
Published U.S. Patent Application Number US-2004-0235953-A1, published Nov. 25, 2004.
PCT International Patent Application Publication No. WO 2005/082042, published Sep. 9, 2005.
U.S. Pat. No. 6,343,382.
U.S. Pat. No. 6,743,823.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of treating a subject at risk for vasospasm associated with aneurysmal subarachnoid hemorrhage and relative hypocitrullinemia comprising intravenously administering to the subject suffering from aneurysmal subarachnoid hemorrhage and relative hypocitrullinemia an amount of citrulline effective to raise the subject's plasma citrulline level to over 37 µmol/liter, whereby the risk of vasospasm is reduced.

2. The method of claim 1, wherein the subject has suffered from trauma.

3. The method of claim 1, wherein the subject has atherosclerosis.

4. The method of claim 3, wherein the atherosclerosis is associated with coronary arterial disease, carotid arterial disease, peripheral arterial disease, or a combination thereof.

5. The method of claim 1, wherein the citrulline is administered in a dose ranging from about 100 mg to about 30,000 mg.

6. The method of claim 5, wherein the citrulline is administered in a dose ranging from about 250 mg to about 1,000 mg.

7. The method of claim 1, wherein the citrulline is administered in a dose of about 100 mg/kg, 200 mg/kg, 400 mg/kg, 600 mg/kg, or 800 mg/kg.

* * * * *